(12) United States Patent
Kim

(10) Patent No.: US 12,396,887 B2
(45) Date of Patent: Aug. 26, 2025

(54) OPHTHALMIC TREATMENT DEVICE AND METHOD FOR DRIVING SAME

(71) Applicant: LUTRONIC CORPORATION, Goyang-si (KR)

(72) Inventor: Jong Min Kim, Seoul (KR)

(73) Assignee: LUTRONIC CORPORATION, Goyang-si (KR)

( * ) Notice: Subject to any disclaimer, the term of this patent is extended or adjusted under 35 U.S.C. 154(b) by 0 days.

(21) Appl. No.: 18/501,946

(22) Filed: Nov. 3, 2023

(65) Prior Publication Data

US 2024/0074901 A1 Mar. 7, 2024

Related U.S. Application Data

(63) Continuation of application No. 17/158,512, filed on Jan. 26, 2021, now Pat. No. 11,833,079, which is a
(Continued)

(30) Foreign Application Priority Data

Jul. 30, 2014 (KR) ........................ 10-2014-0097481

(51) Int. Cl.
*A61F 9/008* (2006.01)
*A61F 9/00* (2006.01)
*A61N 5/06* (2006.01)

(52) U.S. Cl.
CPC ................ *A61F 9/008* (2013.01); *A61F 9/00* (2013.01); *A61F 9/00821* (2013.01); *A61N 5/06* (2013.01);
(Continued)

(58) Field of Classification Search
CPC .. A61F 9/008; A61F 9/00821; A61F 9/00844; A61F 9/00851; A61F 9/00863;
(Continued)

(56) References Cited

U.S. PATENT DOCUMENTS 4,881,808 A * 11/1989 Bille ........................ A61F 9/008
606/5
6,004,314 A 12/1999 Wei et al.
(Continued)

FOREIGN PATENT DOCUMENTS

EP 0 697 611 A2 2/1996
JP 2006-517028 A 7/2006
(Continued)

OTHER PUBLICATIONS

Extended European Search Report for EP Application No. 15828054.5, dated Apr. 4, 2018.
Office Action dated Jan. 6, 2023 for U.S. Appl. No. 17/158,512.

*Primary Examiner* — Ahmed M Farah

(57) ABSTRACT

The present invention relates to an ophthalmic treatment device and a method for operating the same. The present invention provides an ophthalmic treatment device and a method for operating the same, the ophthalmic treatment device comprising: a treatment beam generation unit for generating a treatment beam; a beam delivery unit for forming a path along which the treatment beam generated from the treatment generation unit is delivered to a treatment area positioned on the fundus; a monitoring unit for emitting a detecting beam along the path of delivery of the treatment beam and sensing treatment area state information on the basis of information regarding a change in speckle of the detecting beam, which is scattered and reflected from the treatment area; and a control unit for controlling the driving of the treatment beam generation unit on the basis of the treatment area state information sensed by the monitoring unit.

15 Claims, 12 Drawing Sheets

Related U.S. Application Data continuation of application No. 15/500,451, filed as application No. PCT/KR2015/007994 on Jul. 30, 2015, now Pat. No. 10,898,376.

(52) U.S. Cl.
CPC .. *A61N 5/0616* (2013.01); *A61F 2009/00844* (2013.01); *A61F 2009/00851* (2013.01); *A61F 2009/00863* (2013.01); *A61F 2009/0087* (2013.01); *A61F 2009/00872* (2013.01); *A61F 2009/00897* (2013.01)

(58) Field of Classification Search
CPC ............... A61F 9/0087; A61F 9/00872; A61F 9/00897; A61N 5/06; A61N 5/0616; A61N 2005/0626; A61N 2005/065; A61N 5/067
USPC .............................................................. 606/4
See application file for complete search history.

(56) References Cited

U.S. PATENT DOCUMENTS

| | | |
|---|---|---|
| 6,312,422 B1 | 11/2001 | Dubnack |
| 7,792,249 B2 | 9/2010 | Gertner et al. |
| 10,420,676 B2 | 9/2019 | Kim |
| 10,485,703 B2 | 11/2019 | Nomura et al. |
| 10,588,781 B2 | 3/2020 | Kim et al. |
| 10,898,376 B2 | 1/2021 | Kim |
| 11,382,792 B2 | 7/2022 | Kim |
| 2006/0217691 A1* | 9/2006 | Schuele ............... A61F 9/008 606/4 |
| 2006/0233216 A1 | 10/2006 | Schuele |
| 2007/0185475 A1 | 8/2007 | Frey et al. |
| 2009/0093798 A1* | 4/2009 | Charles ............... A61F 9/00823 606/4 |
| 2009/0275929 A1* | 11/2009 | Zickler ............... A61B 3/113 606/4 |
| 2011/0238046 A1 | 9/2011 | Dick et al. |
| 2013/0261612 A1 | 10/2013 | Yokosuka et al. |
| 2015/0366705 A1* | 12/2015 | Ha ......................... A61F 9/008 606/6 |
| 2016/0302969 A1 | 10/2016 | Yamamoto |
| 2016/0331585 A1 | 11/2016 | Kim |
| 2017/0266041 A1 | 9/2017 | Kim |

FOREIGN PATENT DOCUMENTS

| | | |
|---|---|---|
| JP | 2009-523556 A | 6/2009 |
| JP | 2012-213634 A | 11/2012 |
| KR | 10-2014-0009846 A | 1/2014 |

\* cited by examiner

OPHTHALMIC TREATMENT DEVICE AND METHOD FOR DRIVING SAME

CROSS-REFERENCE TO RELATED APPLICATIONS

The present application is a continuation of U.S. patent application Ser. No. 17/158,512, filed Jan. 26, 2021, which is a continuation of U.S. patent application Ser. No. 15/500,451, filed Jan. 30, 2017, now issued as U.S. Pat. No. 10,898,376, which is a U.S. National Stage of International Patent Application No. PCT/KR2015/007994 filed Jul. 30, 2015, which claims priority to and the benefit of Korean Patent Application No. 10-2014-0097481 filed in the Korean Intellectual Property Office on Jul. 30, 2014, the entire contents of which are incorporated herein by reference.

TECHNICAL FIELD

The present invention relates to a laser treatment device and a method of driving the same, and more particularly, to an ophthalmic treatment device and a method of driving the same that detect a state of a treatment area in which a treatment is performed and that control treatment contents.

Background Art

Nowadays, technology is widely used that performs a treatment with a method of changing a tissue state by light energy absorbed to a human body tissue by radiating light to a human body. Particularly, a treatment device using laser is widely used for various lesions such as skin disease, eye disease, nerve disease, joint disease, and gynecology disease.

Particularly, as an ophthalmic treatment device using laser, a plurality of devices for treating an anterior segment lesion of eye such as keratoplasty, glaucoma, or cataract operation have been developed, and nowadays, a device for treating various lesions of a fundus area as well as macular degeneration has been developed. Such an operation device is disclosed in Korean Patent Laid-Open Publication No. 10-2014-0009846.

In this way, when performing a treatment with an ophthalmic treatment device using light, it is necessary to continuously monitor a state of a position in which the treatment is performed. However, as in a conventional case, when using ultrasonic waves or an optical sensor such as a Charged Coupled Device (CCD) or a Complementary Metal-Oxide Semiconductor (CMOS), an internal state of a treatment area cannot be monitored or there is a limitation in detecting a micro change of a tissue.

DISCLOSURE

Technical Problem

The present invention provides an ophthalmic treatment device and a method of driving the same that can monitor in real time a state change of the inside of a tissue of a treatment area while performing a treatment and that can perform a treatment based on the monitored state change.

Technical Solution

In accordance with an aspect of the present invention, an ophthalmic treatment device includes: a treatment beam generation unit that generates a treatment beam; a beam delivery unit that forms a path that advances a treatment beam generated by the treatment beam generation unit to a treatment area positioned at a fundus; a monitoring unit that radiates a detecting beam along an advancing path of the treatment beam and that detects speckle pattern information of the detecting beam scattered or reflected from the treatment area to detect state information about the treatment area; and a control unit that controls driving of the treatment beam generation unit based on state information about the treatment area detected in the monitoring unit.

Here, the monitoring unit may detect state information about the treatment area based on interference information of the detecting beam scattered or reflected from the treatment area.

Specifically, while the treatment beam is radiated at a predetermined position, the monitoring unit radiates the detecting beam multiple times to the predetermined position to detect state information about the predetermined position. The monitoring unit may compare state information detected by each detecting beam with state information detected by the previously radiated detecting beam to determine a state change of the treatment area.

Here, the monitoring unit may selectively extract information corresponding to an interest depth region among state information detected by the each detecting beam and compare information about the extracted interest depth region with information about an interest depth region detected by a previously radiated detecting beam to determine whether a state of the treatment area is changed.

In this case, the interest depth region may be an area including an RPE cell layer of the treatment area. Alternatively, a depth corresponding to the interest depth region may be directly set by a user through an interface.

Here, the monitoring unit may detect a temperature change of a treatment area occurring when the treatment beam is absorbed in the treatment area. A characteristic of the light path, along which the detecting beam advances, changes, when a refractive index or a volume of a tissue positioned at the treatment area changes with temperature increase of the treatment area, and the monitoring unit may detect a speckle pattern change according to the light path characteristic change of the detecting beam to detect a temperature change of the treatment area. For example, the monitoring unit may determine that a temperature of the RPE cell continuously increases, if a change amount of a speckle pattern of the reflected detecting beam is in a predetermined range and determine that the RPE cell is necrotized, if a change amount of a speckle pattern of the reflected detecting beam exceeds a predetermined range.

Specifically, the monitoring unit may include: a light source that radiates the detecting beam to a treatment area; a detection unit that detects a speckle pattern of the detecting beam reflected from the treatment area; and a processor that extracts information about a portion adjacent to an RPE cell layer in a speckle pattern detected by the detection unit to determine a state change of a portion adjacent to the RPE cell layer.

The control unit adjusts a magnitude of energy transferred per unit area of a treatment area by the treatment beam based on state information about a treatment area detected by the monitoring unit. The control unit may control the treatment beam generation unit to gradually increase energy transferred per unit area of a treatment area, if a change of state information about the treatment area detected by the monitoring unit is less than or equal to a reference value.

In accordance with another aspect of the present invention, a method of driving an ophthalmic treatment device includes: radiating a treatment beam to a target position by driving a treatment beam generation unit; radiating a detecting beam to a treatment area in which the treatment beam is radiated by driving a monitoring unit and detecting state information about the treatment area based on interference information of the detecting beam reflected from the treatment area; and adjusting, by a control unit, operation of the treatment beam generation unit based on the detected state information.

Here, the detecting of state information about the treatment area may include detecting state information about the treatment area by detecting a speckle pattern of the detecting beam. The detecting of state information about the treatment area may include extracting information corresponding to an interest depth region among interference information by the detecting beam. Specifically, the detecting of state information about the treatment area may include: detecting a speckle pattern from the detecting beam; extracting information about an interest depth region corresponding to an RPE cell layer from the speckle pattern; and determining a speckle pattern change amount of the interest depth region to determine a state change of the treatment area.

Advantageous Effects

According to the present invention, by performing a treatment by detecting state information within a treatment area, an optimized treatment can be performed, and damage due to deterioration of a periphery of the treatment area can be prevented.

Further, by detecting state information using a speckle pattern of a detecting beam, a treatment that reflects a micro state change can be performed, and by extracting and analyzing only information about a specific area among acquired information and by minimizing a time to be consumed for analysis, monitoring similar to real time can be performed.

BEST MODE

Figure 1:
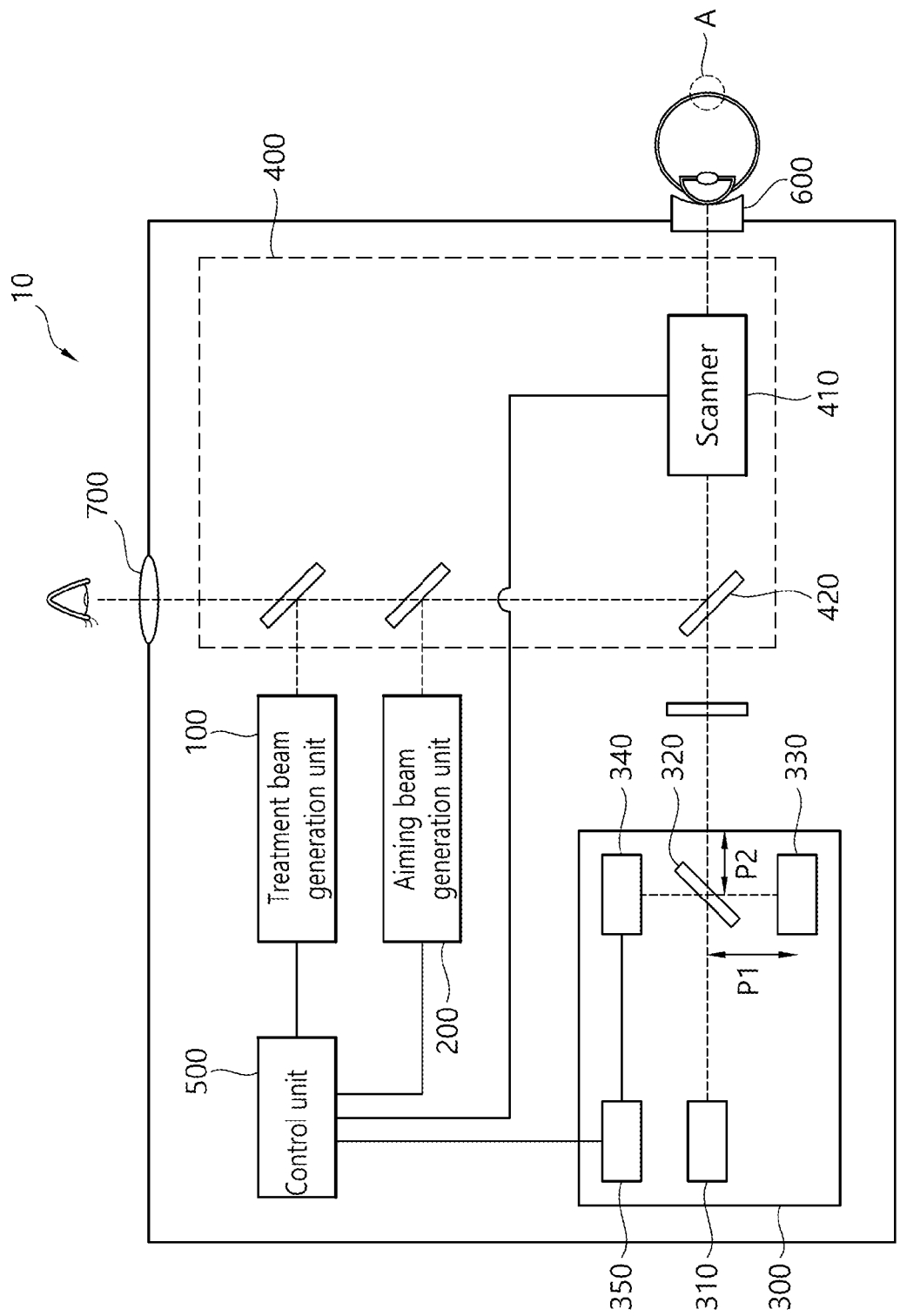
FIG. 1 is a schematic diagram illustrating an ophthalmic treatment device according to an exemplary embodiment of the present invention.

Hereinafter, an ophthalmic treatment device according to an exemplary embodiment of the present invention will be described in detail with reference to the drawings. In the following description, a position relationship of each element will be described based on the drawing. For convenience of description, the drawing may simplify a structure of the invention or may be exaggeratingly displayed, as needed. Therefore, the present invention is not limited thereto and various devices may be added, changed, or omitted.

In the present exemplary embodiment, an example of an ophthalmic treatment device for treating a lesion of a fundus area such as a retina will be described. However, the present invention is not limited thereto and may be applied to a treatment device that treats a lesion other than a fundus area. For example, the present invention may be applied to an ophthalmic treatment device to be used for a treatment of an anterior segment of eye such as a patient's cornea and may be applied to a dermatological treatment device for treating a lesion such as a skin pigment and a blood vessel in addition to an ophthalmic lesion.

FIG. 1 is a schematic diagram illustrating an ophthalmic treatment device according to an exemplary embodiment of the present invention. As shown in FIG. 1, an ophthalmic treatment device 10 according to an exemplary embodiment of the present invention includes a treatment beam generation unit 100 that generates a treatment beam, an aiming beam generation unit 200 that generates an aiming beam, and a beam delivery unit 400 that forms a path in which a treatment beam and an aiming beam advance to a treatment area. Further, the ophthalmic treatment device 10 includes a monitoring unit 300 that detects state information about a treatment area and a control unit 500 that controls driving of the treatment beam generation unit based on information detected in the monitoring unit.

The treatment beam generation unit 100 may include a treatment beam light source that generates a treatment beam and various optical elements that process a characteristic of light generated in the treatment beam light source. The treatment beam is configured with laser, and the treatment beam light source may include a laser medium or a laser diode such as Nd:YAG and Ho:YAG that may oscillate laser. The treatment beam generation unit 100 may include various electric circuits for exciting laser, an optical filter for oscillating light of a specific wavelength among various wavelength bands, and various elements such as a shutter.

The ophthalmic treatment device 10 according to the present exemplary embodiment treats various lesions occurring in a fundus area such as macular degeneration, and a treatment beam selectively provides energy to a specific target position (e.g., RPE cell layer). Therefore, the treatment beam may use laser having a pulse width to be selectively absorbed to melanosome of an RPE cell among various cell layers forming a retina. Specifically, the treatment beam may use laser of a visible ray to near-infrared ray range.

The aiming beam generation unit 200 generates an aiming beam to be radiated to a treatment area. The aiming beam notifies a position in which a treatment beam is to be radiated to an operator before the treatment beam is radiated or while the treatment beam is radiated. The aiming beam has a wavelength of a visible light band, and the operator may determine a treatment area by an aiming beam reflected from the treatment area.

An aiming beam generated in the aiming beam generation unit 200 may be radiated to indicate one spot in which a treatment beam is radiated from the treatment area. Alternatively, an aiming beam may be radiated to indicate a pattern in which a treatment beam is continuously radiated or to simultaneously indicate a plurality of spots.

In addition, an aiming beam may be radiated to form an image of a lattice form or a boundary line form instead of a spot form to display an area in which a treatment beam is to be radiated. In this case, the aiming beam may be radiated along a path different from that of a treatment beam.

However, when an operator can determine a treatment area through a separate interface such as a monitor, the aiming beam generation unit may be omitted.

The beam delivery unit 400 is configured with a plurality of optical elements disposed between the treatment beam generation unit 100 and a contact lens 600 that fixes a patient's eye. The beam delivery unit configures a light path along which a treatment beam radiates. The aiming beam and a detecting beam of a monitoring unit to be described later advance along beam delivery unit. In this case, the aiming beam and the detecting beam may radiate along a path including at least a portion of a light path of the treatment beam. However, the aiming beam or the detecting beam may have a separate light path from that of the treatment beam.

Specifically, as shown in FIG. 1, the beam delivery unit includes a plurality of beam combiners 420. Thereby, a treatment beam, an aiming beam, and a detecting beam each may enter into the beam delivery unit to be radiated to a treatment area. The aiming beam and the detecting beam each reflected from the treatment area may advance in a direction of a lens 700 in which an operator's eye is positioned or may be again applied to the monitoring unit 300 through the beam delivery unit 400.

The beam delivery unit 400 may include a scanner 410 for changing a position at which a beam is radiated. The scanner 410 may include at least one reflection minor and a driver that rotates the at least one reflection minor and change a radiation position of a beam while a rotation position of a reflection mirror that reflects the beam changes.

In addition, the beam delivery unit 400 may further include an optical element (not shown) such as a plurality of optical lens and optical filters for focusing or dispersing light.

In an end portion of the beam delivery unit 400, the contact lens 600 may be provided. The contact lens 600 is a portion that contacts a patient's eye and performs a function of fixing the patient's eye while performing an operation. The contact lens 600 includes a lens in which a beam advances and may include a suction device that fixes a patient's eye in some case.

Figure 2:
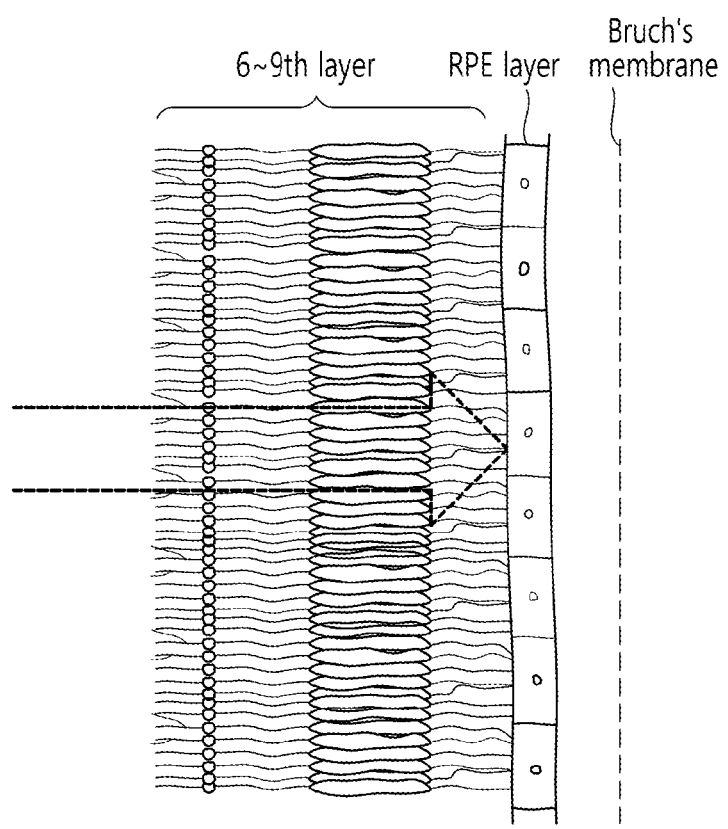
FIG. 2 is an enlarged cross-sectional view of an area A of FIG. 1.

FIG. 2 is an enlarged cross-sectional view of an area A of FIG. 1. FIG. 2A is a diagram illustrating a patient's retina tissue corresponding to a treatment area. Such a retina tissue is generally formed with 10 layers of an internal limiting layer, a nerve fiber layer, a ganglion cell layer, an inner plexiform layer, an inner nuclear layer, an outer plexiform layer, an outer nuclear layer, an external limiting layer, a photo receptor layer, and a retinal pigment epithelial layer (RPE layer).

The RPE cell layer forms a boundary layer of a rear direction among the 10 layers and is formed in a tight junction structure. At a lower portion of the RPE layer, a Bruch's membrane is positioned. Such an RPE layer performs a function of supplying nutrients and oxygen from a blood vessel positioned at a lower portion of the Bruch's membrane to a photo receptor and discharging waste generated in the photo receptor through the Bruch's membrane.

Here, when some RPE cells forming the RPE layer do not perform a normal function, nutrients and oxygen are not regularly supplied to photo receptors of a position corresponding to the RPE cell and thus the photo receptors are necrotized. Therefore, the ophthalmic treatment device according to the present exemplary embodiment radiates a treatment beam to an RPE cell that does not perform a normal function to selectively necrotize the RPE cell, thereby inducting regeneration of a new RPE cell.

Specifically, a treatment beam generated in the treatment beam generation unit 100 has a predetermined wavelength corresponding to a visible ray or near-infrared ray range. Light of a corresponding wavelength is scarcely absorbed but transmitted to a cell layer (first cell layer to ninth cell layer) positioned at the front side of a retina and is absorbed to melanosome existing within an RPE cell of the RPE cell layer. Therefore, as an amount of energy absorbed to melanosome increases with radiation of a treatment beam, a temperature of the melanosome increases and thus thermal damage occurs in a corresponding RPE cell. As a temperature increases, a microbubble occurs at a surface of melanosome, and as the microbubble gradually grows, a corresponding RPE cell selectively necrotizes. At a position of an RPE cell in which thermal damage has occurred, a new RPE cell is regenerated and thus a treatment is performed.

Here, when a treatment beam is excessively much radiated, thermal damage may occur in adjacent RPE cells and photoreceptors as well as an RPE cell to which the treatment beam is radiated. Therefore, the ophthalmic treatment device of the present exemplary embodiment includes the monitoring unit 300, and the monitoring unit 300 detects state information about a treatment area while a treatment is performed.

Referring again to FIG. 1, the monitoring unit 300 radiates a detecting beam to the treatment portion and acquires scattering and speckle pattern information about the treatment portion. The detecting beam arrived at the treatment area through such a beam delivery unit 400 is reflected by mediums of the treatment area to direct backward an traveled path and to be received in the monitoring unit 300.

Here, a detecting beam is configured with light of a wavelength having a property less absorbed to a tissue and having excellent transmittance. While a detecting beam radiated to a treatment area advances from a surface to the inside of a retina, the detecting beam passes through a tissue or an interface having different refractive indexes to be scattered or reflected. Therefore, interference information of the reflected detecting beam may include speckle information about each position while advancing from a surface of the treatment area to an RPE cell layer.

Accordingly, the monitoring unit 300 analyzes an interference information change of the received detecting beam to detect state change information about the treatment area. Here, state change information about the treatment area may include at least one of a temperature change, a volume change, and a refractive index change of a tissue occurring in the treatment area while a treatment beam is radiated, and information on whether cells are moved.

When a treatment beam is radiated to the treatment area, a temperature of a tissue increases and thus a volume of the tissue changes, a tissue characteristic changes, or a partial tissue moves and thus an advancing characteristic of light that passes through the tissue changes (e.g., a light path length, a speckle pattern). Therefore, while a treatment is performed, a characteristic of a reflected detecting beam changes, and the monitoring unit 300 may detect a state change of a treatment area based on a characteristic change of a received detecting beam.

Specifically, the monitoring unit 300 according to the present exemplary embodiment may be configured using an Optical Coherent Tomography (OCT) device. Such an OCT device obtains tomography information about a tissue using interference information of light. A kind of Time Domain OCT (TD OCT), spectral domain OCT (SD OCT), and swept source OCT (SS OCT) may exist according to a drive method and a measurement method, and in the present exemplary embodiment, the SD OCT or the SS OCT may be used. However, conventional OCT acquires tomography information while moving a coordinate in a horizontal direction (B—scan), however in the present exemplary embodiment, tomography information about a tissue can be obtained at the same position through Z-scan without separate B-scan while monitoring a specific treatment position.

As shown in FIG. 1, the monitoring unit 300 includes a light source 310, a beam splitter 320, a reference beam reflector 330, a detection unit 340, and a processor 350.

The light source 310 may be a light source that generates a low coherent beam in SD OCT and may be a swept source light source that may change a wavelength of light in SS OCT.

Light emitted from the light source 310 is divided into two beams of a detecting beam and a reference beam while passing through the beam splitter 320. The reference beam travels to a reference beam reflector direction along a first path P1 and is reflected from the reference beam reflector 330. The detecting beam travels along a second path P2, advances through the beam delivery unit 400 to the treatment area and then is reflected. Portions of the reflected detecting beam and the reference beam are combined in the beam splitter 320 to be applied to the detection unit 340.

Interference occurs in the combined detecting beam and reference beam, and the detection unit 340 may detect speckle state information about a treatment area using interference information of the received detecting beam and reference beam. Here, the detection unit 340 may use an array detector in the SD OCT and use a photo diode in the SS OCT.

When the combined detecting beam and reference beam are applied, such a detection unit 340 may separate the combined detecting beam and reference beam on a wavelength band basis to acquire state information according to a depth of a treatment area using a signal in which a Fourier transform processing is performed. A signal detected by the detection unit 340 may acquire various forms of information about a treatment area according to processing contents, and in the present exemplary embodiment, speckle pattern information of the detecting beam may be acquired.

The speckle pattern means an intensity pattern occurring by mutual interference between rays constituting light. Such a speckle pattern may form different patterns according to a position of a light path, and a surface characteristic of a reflection surface and scattering information occurring when light passes through a tissue is reflected to each speckle pattern. When a micro change occurs on a light path, an interference pattern changes between rays and thus a speckle pattern of a corresponding position changes.

In this way, state information about a treatment area is reflected to a speckle pattern of a detecting beam detected by the detection unit 340. Therefore, by detecting a change of a speckle pattern while performing a treatment, it is possible to determine a micro state change of a treatment area such as temperature increase, a change of a tissue thickness, a change of a refractive index, and a tissue movement.

Therefore, the processor 350 analyzes a change of a signal (e.g., speckle pattern) detected by the detection unit 340 to determine a state change of a treatment area. When a state change of the treatment area is detected, in order to change treatment contents by reflecting the state change, the processor 350 may provide state change information to the control unit 500.

Figure 3:
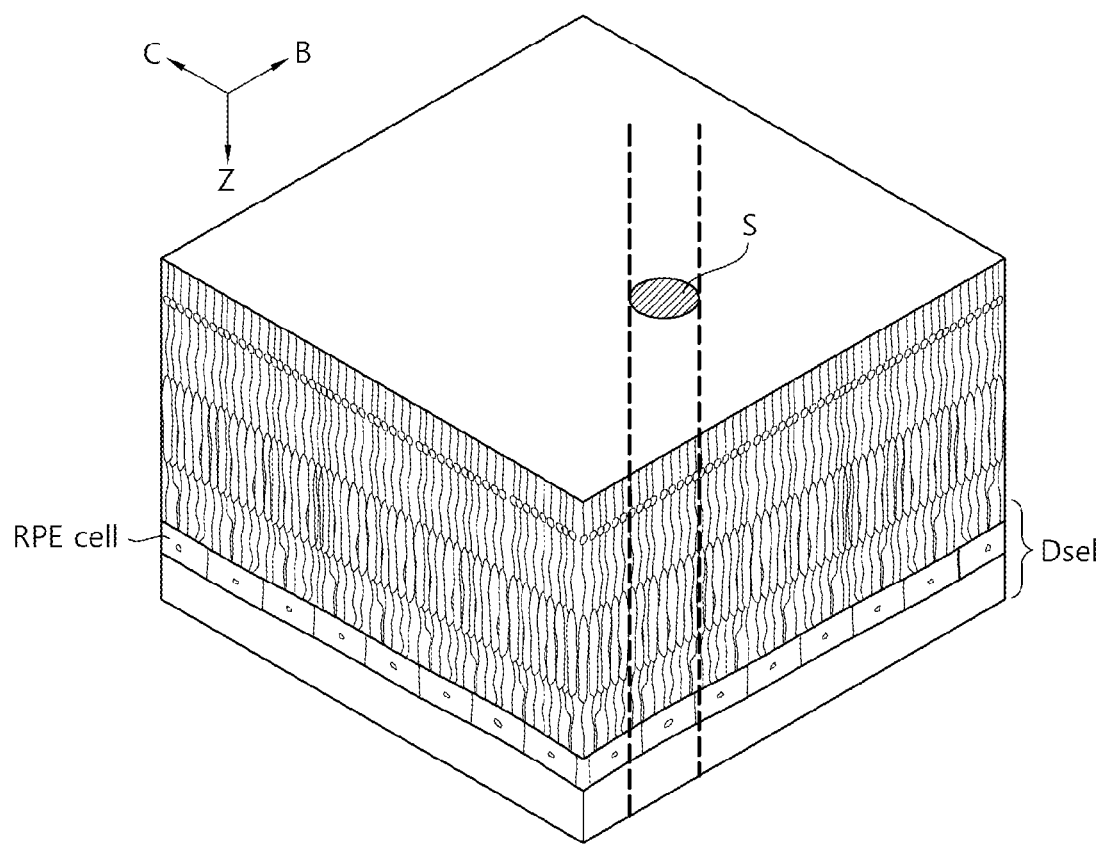
FIG. 3 is a diagram illustrating a tomogram structure in which a treatment beam and a detecting beam are radiated.

FIG. 3 is a diagram illustrating a tomogram structure of a fundus in which a treatment beam and a detecting beam are radiated. As described above, the monitoring unit 300 radiates a detecting beam to a treatment area S while a treatment is performed and detects a state information change of a treatment area using the reflected detecting beam (see FIG. 3).

More specifically, while a treatment is performed, the light source 310 radiates a detecting beam multiple times to the treatment area S. The detection unit 340 continuously detects a signal by the reflected detecting beam. A signal obtained from the detection unit by the detecting beam includes state information about the treatment area at a corresponding time point. Therefore, the monitoring unit 300 according to the present exemplary embodiment may acquire in real time state information about the treatment area while performing a treatment.

The processor 350 may detect whether a state of the treatment area is changed with a method of comparing a signal detected by each detecting beam. For example, the processor 350 may determine whether a state is changed with a signal detected by the detection unit 340 by each detecting beam (e.g., n-th detecting beam) and a signal detected by a previously radiated detecting beam (e.g., (n−1)th detecting beam) based on a value analyzed with cross correlation. Alternatively, the processor 350 may determine whether a state of a signal detected by each detecting beam and a signal detected by a detecting beam (e.g., a first detecting beam) to be a reference is changed based on a value analyzed with cross correlation. In the present exemplary embodiment, a signal to be a target that calculates cross correlation is a speckle pattern signal detected by the detection unit, but various forms of signals may be used.

Figure 4:
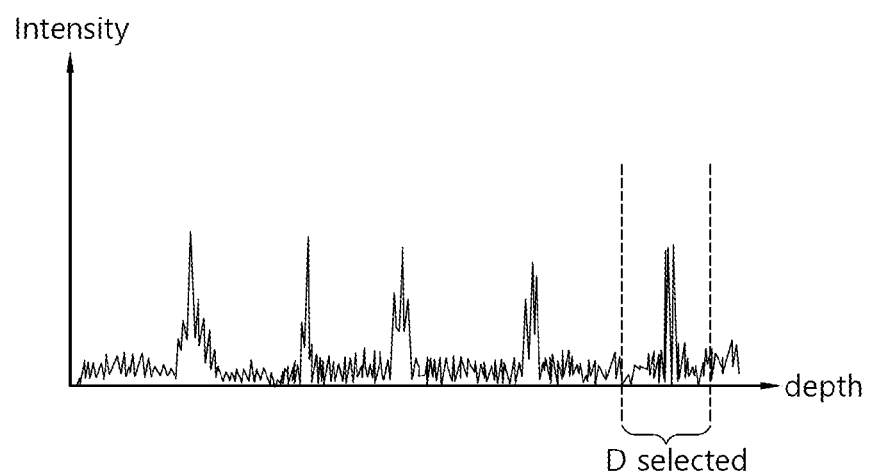
FIG. 4 is a graph illustrating an example of a signal detected by a detection unit.

FIG. 4 is a graph illustrating an example of a signal acquired in a processor. Here, a signal detected by a detection unit includes information about an entire depth of a fundus corresponding to an advancing path of a detecting beam. Specifically, a signal acquired by one detecting beam may include entire state information about a photoreceptor layer, an RPE cell layer, and a Bruch's membrane layer from a retina surface (see FIG. 3). Therefore, in the present exemplary embodiment, in a signal detected by the detection unit, only information about a specific concern area (hereinafter, referred to as a 'interest depth region') Dsel is selectively extracted and it may be detected whether a state is changed based on the extracted information about the interest depth region.

Specifically, when a signal is detected by any one detecting beam, only information about a specific concern area Dsel is extracted. The processor 350 may determine whether a state of information about an interest depth region by a current detecting beam (e.g., nth detecting beam) and information about an interest depth region by a previously radiated detecting beam (e.g., (n−1) th detecting beam) is changed by cross correlation (here, while the detecting beam is continuously radiated, in a state in which B-scan is not performed, the detecting beam is radiated to the same position).

In this case, a calculation amount that should process remarkably reduces and thus fast calculation can be performed, compared with a calculation processing using an entire detected signal. Therefore, by minimizing a time to be consumed in analyzing state information, monitoring similar to real time can be performed.

Further, when performing calculation that detects a change between a previous signal and a current signal, if a comparison is performed by selecting only a signal of an interest depth region in which a state change most actively represents, a change rate is remarkably largely represented, compared with a case of comparing an entire signal. Therefore, it may be accurately determined whether a state of a treatment area is changed.

Here, the interest depth region Dsel may be a tissue to be a target while performing a treatment, a tissue in which a state change earliest occurs, or a depth region in which a tissue having a large state change amount is positioned. In the ophthalmic treatment device 10 according to the present exemplary embodiment, as described above, a most treatment beam is absorbed to an RPE cell layer and thus while a temperature of the RPE cell layer increases, a state thereof is changed and thus in the present exemplary embodiment, the interest depth region may be set to a depth including the RPE cell layer. For example, an area from 50% point to 100% point of a thickness from a retina surface in an outside direction (low direction of FIG. 3) may be set to an interest depth region, and more specifically, an area from 70% point to 100% point of a retina thickness from a retina surface may be set to an interest depth region.

In the present exemplary embodiment, because a device that treats a lesion of a fundus area is described, an RPE cell layer and an adjacent area are set to an interest depth region, but various applications may be performed. For example, when treating a cornea, a specific depth region within a stroma may be set to an interest depth region, and an interest depth region may be differently set according to a treatment lesion.

Such an interest depth region Dsel may use a predetermined value, but in the present exemplary embodiment, a user may set an interest depth region Dsel through an interface (not shown) in consideration of a treatment lesion and a patient's characteristic. Because a state and a thickness of a retina are different according to a patient, an interest depth region may be set in consideration of a patient's retina tomography image photographed when performing checkup.

In this way, the processor 350 compares a signal of an extracted interest depth region Dsel to determine a state change of a treatment area, and such a determination method may be configured with various methods.

For example, if a change amount of an extracted signal is equal to or less than a predetermined value (first predetermined value), compared with a previous signal, it may be determined that a state of the treatment area is not changed, and if a change amount is larger than a predetermined value, it may be determined that a state of a treatment area is changed.

In another example, as described above, when a temperature of the RPE cell increases with radiation of a treatment beam, while a microbubble occurs, a volume of the RPE cell gradually expands. Therefore, in this way, while a temperature of the RPE cell sequentially increases, a detection signal sequentially changes. At a time point (e.g., a destruction time point of the RPE cell) at which the RPE cell necrotizes with a continuous treatment, the detection signal may discontinuously change. Therefore, if a change amount of an extracted signal is equal to or less than a predetermined value (second predetermined value), the processor 350 may determine to continuously increase a temperature in a state in which the RPE cell does not necrotize, and if a change amount of an extracted signal is larger than a predetermined value, the processor 350 may determine that the RPE cell is necrotized.

In another example, the processor 350 may compare a change amount of an extracted signal with previously stored reference data, determine a temperature of the treatment area, and estimate and determine a state change of a treatment area based on the determined temperature. While a treatment beam is radiated, before a necrosis time point (thermal damage occurrence time point) of the RPE cell, even if a temperature continuously increases, a change amount of the detected signal is minute, but a signal change detected at a necrosis time point rapidly occurs. Therefore, before the RPE cell is necrotized, it is difficult to estimate a necrosis time point of the RPE cell or to adjust treatment contents in consideration of a temperature of the RPE cell. Therefore, the ophthalmic treatment device may have a signal value (or a change amount of a signal) detected by a detecting beam and reference data about temperature information corresponding thereto. The processor may compare a signal detected by a detecting beam with reference data while performing a treatment, determine temperature information of an interest depth region in real time, and control treatment contents in consideration of the temperature information.

In this way, by selectively extracting and processing signal information corresponding to a depth of an interest depth region Dsel, particularly a RPE cell, the monitoring unit 300 according to the present exemplary embodiment may detect state information about the RPE cell while performing a treatment. Particularly, the monitoring unit 300 may monitor a micro state change during a time period in which a temperature increases in a treatment process as well as information about a time point in which a treatment of the RPE cell is complete while performing a treatment. Therefore, according to the present exemplary embodiment, an adjacent tissue may be prevented from being thermally damaged due to excessive radiation of a treatment beam, and by accurately transferring energy of a desired amount, an optimal treatment can be performed.

The control unit 500 controls operation of various constituent elements such as the treatment beam generation unit 100, the aiming beam generation unit 200, and the beam delivery unit 400. In this case, state information about a treatment area detected by the monitoring unit 300 is transferred to the control unit 500, and the control unit 500 may control various constituent elements based on state information about a treatment area.

The control unit 500 may control operation of the treatment beam generation unit 100 according to state information about a treatment area. For example, the control unit 500 may variously control treatment beam parameters such as an output of a treatment beam, a pulse time of a treatment beam, a time between pulses constituting a treatment beam, or a focus level of a treatment beam.

In this way, the monitoring unit monitors a treatment process and the control unit adjusts treatment contents in consideration of the monitored treatment process and thus the ophthalmic treatment device 10 according to the present exemplary embodiment may perform an optimal treatment. The control of treatment contents in consideration of a treatment process may be designed with various methods, and hereinafter, as an example, a method of driving an ophthalmic treatment device according to the present exemplary embodiment will be described.

Figure 5:
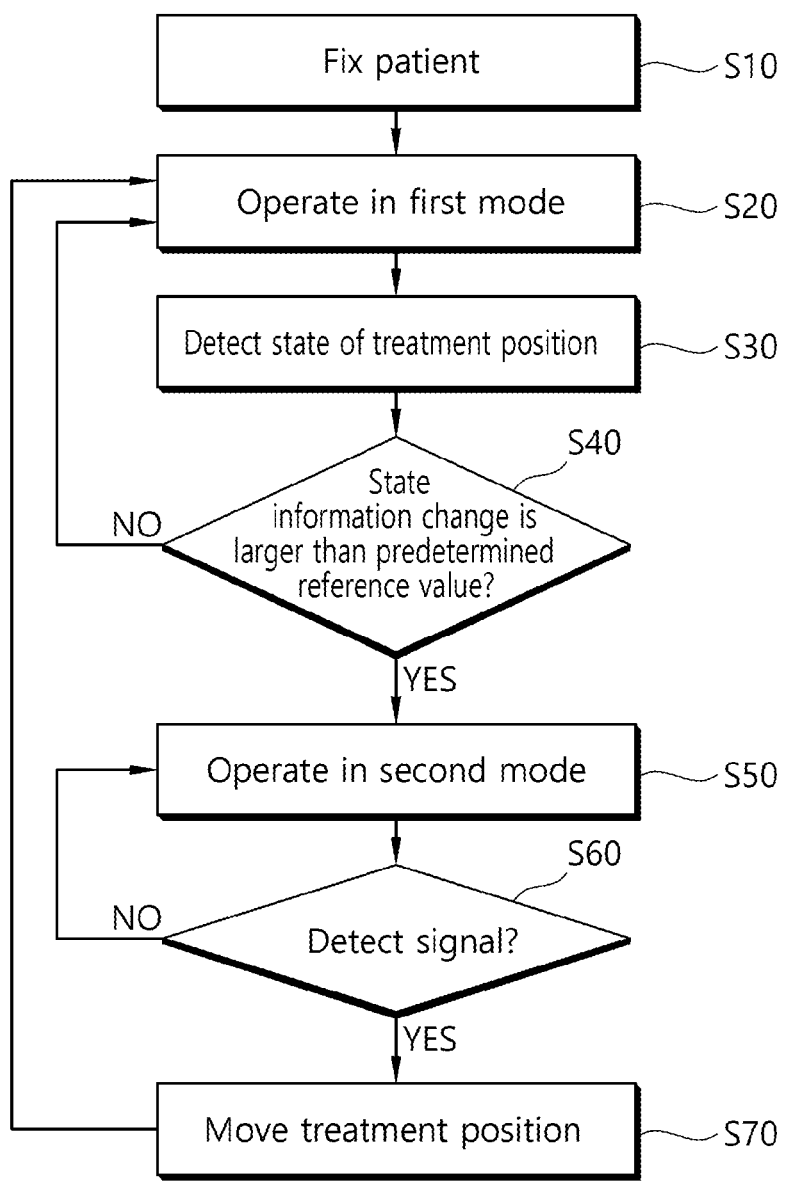
FIG. 5 is a flowchart illustrating a method of driving the ophthalmic treatment device of FIG. 1.

FIG. 5 is a flowchart illustrating a method of driving the ophthalmic treatment device of FIG. 1. When a treatment area is determined according to a checkup result of a patient's lesion, the patient eyeball is fixed to the contact lens 600 (S10).

The control unit 500 drives the treatment beam generation unit 100 to radiate a treatment beam to the patient's fundus fixed to the contact lens 600 in a first mode M1 (S20). In the first mode, the treatment beam is radiated multiple times and is radiated in a pattern sequentially increasing from energy of a low magnitude provided to a unit area of a treatment area per unit time. Thereby, the control unit 500 can prevent an adjacent tissue from being damaged by transferring excessive energy to the treatment area.

While the foregoing step is performed, the monitoring unit 300 radiates a detecting beam to a position in which a treatment beam is radiated multiple times and receives the reflected detecting beam to continuously detect a state of the treatment area (S30). In this case, each detecting beam may be controlled to be radiated simultaneously with the treatment beam or a detecting beam and a treatment beam may be controlled to be alternately radiated.

Figure 6:
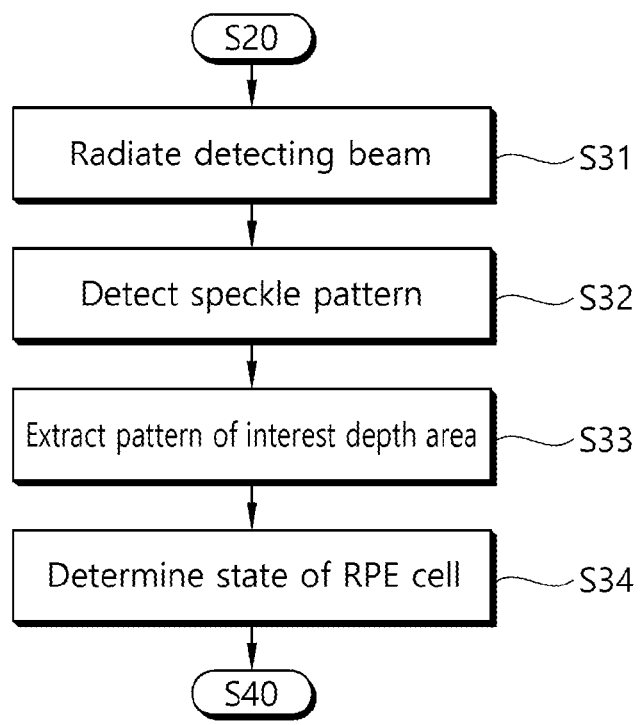
FIG. 6 is a flowchart illustrating step of detecting a state of a treatment area in FIG. 5.

FIG. 6 is a flowchart illustrating step of detecting a state of a treatment area in FIG. 5. Hereinafter, the step will be described in more detail with reference to FIG. 6.

A light source of the monitoring unit 300 radiates a detecting beam to a treatment area in which a treatment beam is radiated (S31). The radiated detecting beam advances to the inside of a retina corresponding to the treatment area and is scattered or reflected.

The detection unit 340 detects a speckle pattern of a detecting beam from interference information of the scattered or reflected detecting beam and a reference beam (S32). Here, the speckle pattern of the detecting beam may include information according to each depth of a retina tomography through which the detecting beam is passed.

The detection unit 340 extracts a speckle pattern of an interest depth region, i.e., a partial area including an RPE cell layer among the detected speckle pattern (S33). The RPE cell layer is an area in which a state change most sensitively occurs by a treatment beam. Therefore, the detection unit 340 or the processor 350 excludes information about an unnecessary depth region in the speckle pattern of the detecting beam and extracts speckle pattern information about a concern RPE cell layer.

The processor 350 determines a state of a treatment area, specifically a state of the RPE cell layer of a treatment area based on the extracted speckle pattern change information about the RPE cell layer (S34). In this case, the processor 350 detects a state of a treatment area with a method of detecting a change amount of speckle pattern information about the RPE cell layer by this detecting beam (e.g., n-th detecting beam) and speckle pattern information about the RPE cell layer by a previous detecting beam (e.g., (n−1) th detecting beam) by cross correlation. Alternatively, a state of a treatment area may be detected with a method of detecting a change amount of speckle pattern information about an RPE cell layer by this detecting beam (e.g., n-th detecting beam) and speckle pattern information about an RPE cell layer by an initial detecting beam (e.g., first detecting beam) by cross correlation.

FIG. 6 illustrates step by one detecting beam of a plurality of detecting beams radiated in a monitoring process, but at this step, while a plurality of detecting beams are radiated, by repeatedly performing the steps S31 to S34 for an entire detecting beam, state information about an RPE cell layer of a treatment area may be continuously detected while performing a treatment.

Referring again to FIG. 6, when state information about the treatment area detected through the foregoing step is detected, the control unit 500 determines whether a state information change is larger than a predetermined reference value (S40). At this step, it is determined whether a change amount of a speckle pattern performed at the foregoing step is larger than a predetermined reference value. Here, a reference value may be variously designed according to treatment contents. For example, a reference value may be set in consideration of a change amount when thermal damage occurs in a treatment area or may be set in consideration of a corresponding change amount when a treatment area arrives at a specific temperature.

Through this step, if state information about a treatment area is equal to or less than a reference value, the control unit 500 may control to maintain a treatment in a current first mode M1. However, if state information about a treatment area exceeds a reference value, the control unit 500 may convert a mode of the treatment beam generation unit to a second mode M2 to control the treatment beam generation unit to operate in the second mode M2 (S50).

Figure 7A:
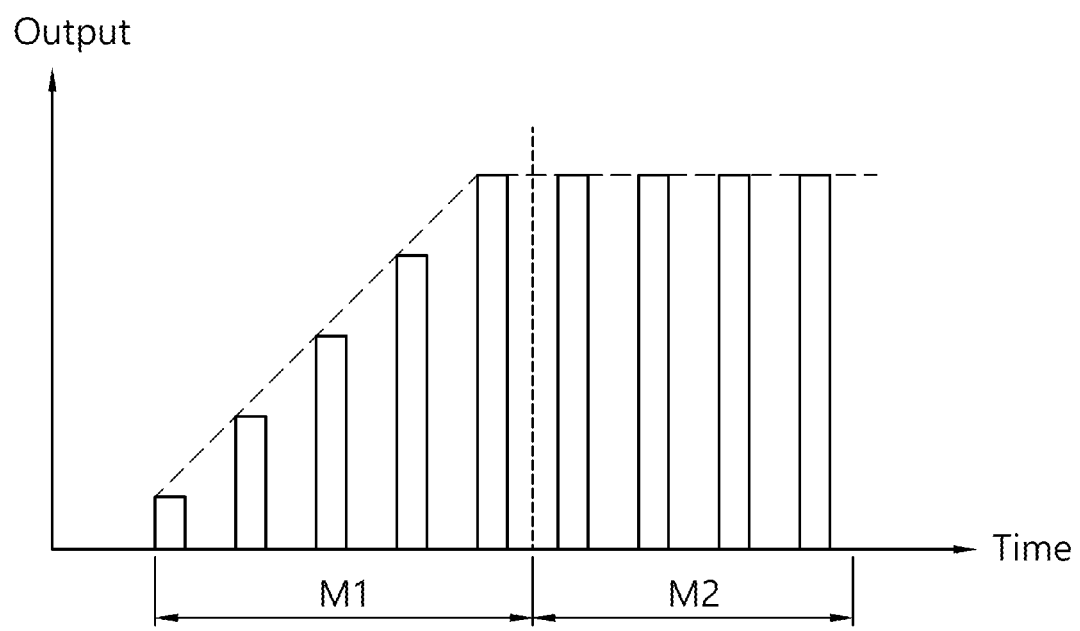
FIG. 7A and FIG. 7B are graphs illustrating examples of a first mode operation and a second mode operation in FIG. 5.
Figure 7B:
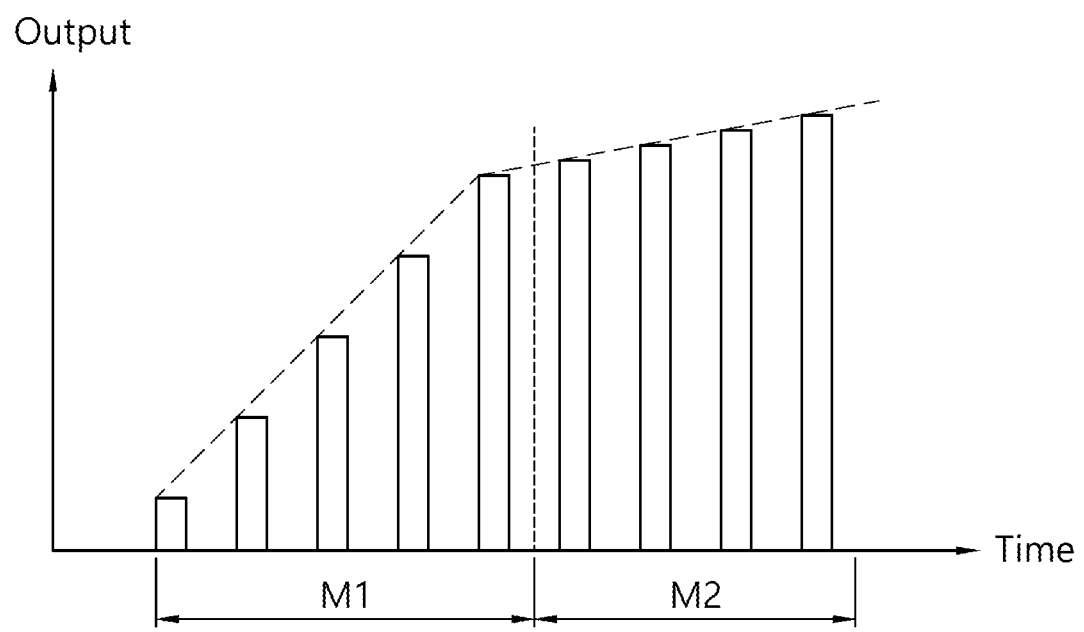

FIG. 7A and FIG. 7B are graphs illustrating examples of a first mode operation and a second mode operation in FIG. 5. As described above, in the first mode M1, the treatment beam generation unit 100 generates a treatment beam such that energy transferred to a unit area of a treatment area per unit time sequentially increases. However, in the second mode M2, it is determined that a temperature of a RPE cell increases to a temperature adjacent to a predetermined temperature, energy transferred to an unit area of a treatment area per unit time increases no longer, and a treatment beam may be generated to maintain a current state (FIG. 7A). Alternatively, a treatment beam may be generated to reduce an increase width of energy transferred to a unit area, compared with the first mode (FIG. 7B).

In this way, even while a treatment beam is radiated in the second mode M2, the monitoring unit 300 monitors state information about a treatment area based on a continuously detected signal. The monitoring unit 300 continuously determines whether a signal (e.g., a signal corresponding to necrosis of the RPE cell) is detected representing whether the RPE cell arrives at a predetermined temperature.

Through the above process, until a treatment completion signal is detected, operation of the second mode M2 may be continued, and at a time point at which a treatment completion signal is detected, radiation of a treatment beam to a corresponding treatment area may be terminated and a treatment may be performed in other treatment areas by changing a treatment beam radiation position to a next treatment area.

When performing the foregoing method of driving the ophthalmic treatment device, in the control of the first mode M1 that sequentially increases energy transferred to a unit area of a treatment area per unit time, in shown in FIG. 7A and FIG. 7B, the first mode M1 was controlled with a method of sequentially increasing an output of a pulse of a treatment beam. However, this is an example and the first mode may be implemented by controlling other variables other than an output of a treatment beam.

Figure 8A:
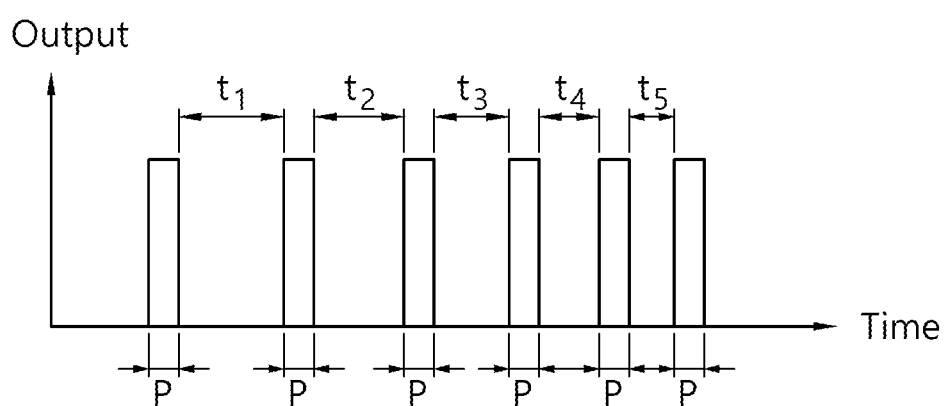
FIG. 8A, FIG. 8B, FIG. 8C, and FIG. 8D are graphs illustrating examples of a first mode operation of FIG. 5 according to another exemplary embodiments of the present invention.
Figure 8B:
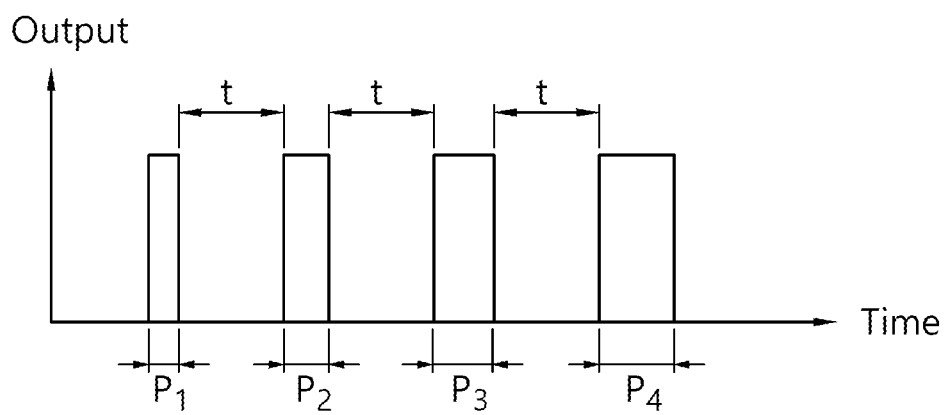
Figure 8C:
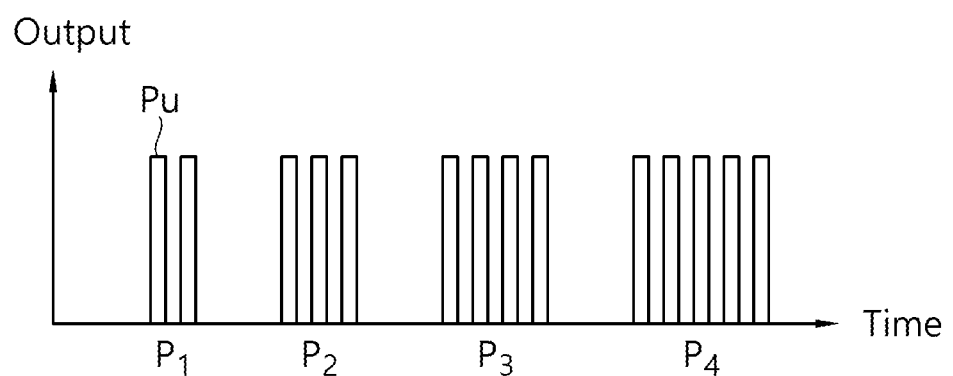
Figure 8D:
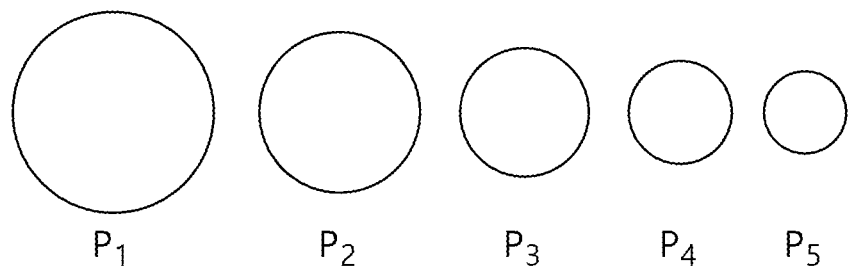

FIGS. 8A to 8D are graphs illustrating examples of a first mode operation of FIG. 5 according to another exemplary embodiments of the present invention. For example, as shown in FIG. 8A, the treatment beam generation unit generates a pulse of the same output having the same pulse duration time, but by gradually reducing an off time between each pulse, the treatment beam generation unit may sequentially increase a magnitude of energy transferred per unit area. Alternatively, as shown in FIG. 8B, the treatment beam generation unit generates a pulse of the same output, but by gradually increasing a pulse duration time of each pulse, the treatment beam generation unit may sequentially increase a magnitude of energy transferred per unit area. In addition, the first mode and the second mode may be implemented with various methods such as a method of radiating one pulse of a treatment beam into a plurality of unit pulses having the same output, but of sequentially increasing the number of a unit pulse constituting one pulse, as shown in FIG. 8C or a method of sequentially increasing a magnitude of energy transferred per unit area of a treatment area with a method of gradually focusing a treatment beam, as shown in FIG. 8D.

Further, in the method of operating an ophthalmic treatment device, it has been described that treatment contents are controlled in two modes according to state information about a treatment area, but for convenience of description, a simple example is described, and variously changes and designs may be performed according to a patient's lesion contents and treatment area.

Further, in the present exemplary embodiment, a signal detected in the monitoring unit was used for only monitoring a state of a treatment area, but a separate display may be provided, and by displaying a tomography image of a treatment area in the display, a user may directly determine an RPE cell state of the treatment area while performing a treatment.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. An optical treatment device, comprising:
a treatment beam generation unit that generates a treatment beam;
a beam delivery unit that forms a path along which the treatment beam radiates to a treatment area of a patient; and
a monitoring unit that radiates a detecting beam to the treatment area and that detects state information of the treatment area based on interference information of the detecting beam scattered or reflected from the treatment area,
wherein, while the treatment beam is radiated to one treatment position, the monitoring unit radiates the detecting beam multiple times to the treatment position to detect state information of the treatment position, and
wherein the monitoring unit selectively extracts information corresponding to an interest depth region among state information detected by each detecting beam and compares the extracted information about the interest depth region with information about the interest depth region detected by a previously radiated detecting beam to determine whether a state of the treatment area is changed.

2. The optical treatment device of claim 1, wherein the monitoring unit radiates the detecting beam multiple times to the treatment position without capturing a B-scan image.

3. The optical treatment device of claim 1, wherein the treatment beam is radiated multiple times to the treatment position and the monitoring unit radiates the detecting beams multiple times correspondingly to radiation of the treatment beam.

4. The optical treatment device of claim 1, wherein the monitoring unit detects light intensity distribution pattern information of the detecting beam scattered or reflected from the treatment area to detect state information of the treatment area.

5. The optical treatment device of claim 1, wherein the monitoring unit compares state information detected by each detecting beam with state information detected by the previously radiated detecting beam to determine a state change of the treatment area.

6. The optical treatment device of claim 1, wherein the interest depth region encompasses a depth region in which a retinal pigment epithelial (RPE) cell layer is positioned within the treatment area.

7. The optical treatment device of claim 1, wherein a depth corresponding to the interest depth region is directly set by a user through an interface.

8. The optical treatment device of claim 1, wherein the monitoring unit detects a temperature change of the treatment area occurring while the treatment beam is absorbed in the treatment area.

9. The optical treatment device of claim 1, wherein a characteristic of a light path along which the detecting beam radiates is changed as a refractive index or a volume of a tissue positioned at the treatment area changes with temperature increase of the treatment area, and
wherein the monitoring unit detects a temperature change of the treatment area by detecting a light intensity distribution pattern change of the detecting beam caused by the change of the characteristic of the light path.

10. The optical treatment device of claim 9, wherein the monitoring unit determines that a temperature of a retinal pigment epithelial (RPE) cell continuously increases, if change amount of the speckle pattern of the reflected detecting beam is in a predetermined range, and determines that the RPE cell is necrotized, if a change amount of the light intensity distribution pattern of the reflected detecting beam exceeds the predetermined range.

11. The optical treatment device of claim 1, further comprising a control unit that controls operation of the treatment beam generation unit based on the state information of the treatment area detected in the monitoring unit.

12. The optical treatment device of claim 11, wherein the control unit adjusts a magnitude of energy transferred per unit area of the treatment area by the treatment beam based on state information about the treatment area detected by the monitoring unit.

13. The optical treatment device of claim 12, wherein the control unit controls the treatment beam generation unit to gradually increase energy transferred per unit area of the treatment area until a value of the state information detected by the monitoring unit reaches a reference value.

14. The optical treatment device of claim 1, wherein the monitoring unit comprises an interferometer.

15. The optical treatment device of claim 1, wherein the state information of the treatment area is extracted by comparing intensity information of phase information or both intensity information and phase information of the interference information of the multiple of detecting beam scattered or reflected from a treatment area.

* * * * *